US010993737B2

(12) United States Patent
Vetter

(10) Patent No.: US 10,993,737 B2
(45) Date of Patent: May 4, 2021

(54) EXCISIONAL DEVICES AND METHODS

(71) Applicant: Transmed7, LLC, Portola Valley, CA (US)

(72) Inventor: James W Vetter, Portola Valley, CA (US)

(73) Assignee: Transmed7, LLC, Portola Valley, CA (US)

( * ) Notice: Subject to any disclaimer, the term of this patent is extended or adjusted under 35 U.S.C. 154(b) by 134 days.

(21) Appl. No.: 15/987,679

(22) Filed: May 23, 2018

(65) Prior Publication Data

US 2019/0357932 A1 Nov. 28, 2019

(51) Int. Cl.
| A61B 17/3207 | (2006.01) |
| A61F 2/95 | (2013.01) |
| A61M 25/10 | (2013.01) |
| A61B 17/00 | (2006.01) |

(52) U.S. Cl.
CPC ............ *A61B 17/3207* (2013.01); *A61F 2/95* (2013.01); *A61M 25/104* (2013.01); *A61B 2017/00893* (2013.01); *A61B 2017/320741* (2013.01); *A61B 2017/320766* (2013.01)

(58) Field of Classification Search
CPC . A61B 10/0233; A61B 10/0266; A61B 10/04; A61B 10/06; A61B 2010/0208; A61B 2010/0225; A61B 2010/045; A61B 17/3205; A61B 17/3207; A61B 2017/320064
See application file for complete search history.

(56) References Cited

U.S. PATENT DOCUMENTS

| 5,807,277 A | 12/1998 | Swaim | |
| 6,391,043 B1 | 5/2002 | Moll et al. | |
| 8,894,653 B2* | 11/2014 | Solsberg | A61B 10/0275 606/79 |
| 2003/0208153 A1* | 11/2003 | Stenzel | A61B 17/3468 604/60 |
| 2009/0306689 A1 | 12/2009 | Welty et al. | |
| 2014/0142602 A1 | 5/2014 | Poloi | |
| 2016/0206340 A1* | 7/2016 | Vetter | A61B 17/3207 |

OTHER PUBLICATIONS

International Search Report and Written Opinion of International Searching Authority dated Aug. 27, 2019 in PCT/US19/33763.

\* cited by examiner

*Primary Examiner* — Todd J Scherbel
(74) *Attorney, Agent, or Firm* — Young Law Firm, P.C.

(57) ABSTRACT

A platform device for material excision or removal from vascular structures for either handheld or stereotactic table use may comprise a work element or elements configured to selectively open and close at least one articulable beak or scoopula configured to penetrate and remove intra-vascular materials or obstructions, or follow a central lumen of another device or over a wire in a longitudinal direction. Flush and vacuum tissue transport mechanisms may be incorporated. A single tube or an inner sheath and an outer sheath which may be co-axially disposed relative to a work element may be configured to actuate a beak or beaks or scoopulae and provisions for simultaneous beak or scoopula closing under rotation may be incorporated.

12 Claims, 2 Drawing Sheets

EXCISIONAL DEVICES AND METHODS

BACKGROUND

Embodiments relate to medical devices and methods. More particularly, embodiments relate to hand-held or mounted single or multiple insertion, single or multiple excisional devices and corresponding methods for vascular clearing and restoration applications. Embodiments further relate to improvements over currently used chronic total occlusion removal systems, specifically in providing minimally invasive and more widely capable reliable cardio-vascular excisional devices and methods.

SUMMARY

Embodiments are drawn to various medical devices and methods that may be used for intra-vascular procedures. According to one embodiment, an excisional device may be configured to remove liquids, solids, semi-solids and single or multiple material samples during a single insertion through the skin (percutaneous procedure) into any vascular area of the body. Embodiments may comprise structures and functionality for different phases of a multi-phase vascular clearing or restoration procedure, which may be performed by hand or by device attachment to a stereotactic table stage or Magnetic Resonance Imaging (MRI) stage. Embodiments may also comprise devices configured for insertion through the central lumen of another compatible excisional device. Embodiments of a device, along with associated related subcomponents described herein, may provide the capability to retrieve solid, contiguous and/or fragmented materials as well as liquid and semi-solid tissues for analysis, diagnosis and treatment and exhibit improvements in functionality and performance relative to present devices and methods for clearing chronic total occlusions and other vascular anomalies. Although some embodiments find particular utility in cardio-vascular intervention procedures, other embodiments also find utility in, for instance, urologic and gynecologic applications, and are not limited therefore to vascular applications described, shown and claimed herein. Embodiments and elements thereof may be deployed in interventional procedures in coronaries, including bypass vessels (veins, internal mammary arteries, free radial grafts and in the case of peripheral vessels, synthetic grafts, native and bypass peripheral vessels including carotid arteries, renals, iliacs, femorals, popliteal and trifurcation vessels as well as other distal vessels including venous and arterial vessels in various locations). Embodiments may include atherectomy and thrombectomy devices (those that remove plaque and other components of diseased vessel walls), which also contain a subset that may be used to treat both acute and chronic thromboembolic lesions and another subset that may be used to remove restenotic "scar" tissue obstructions (intimal hyperplastic lesions); chronic total occlusion devices, which include a variety of devices some of which may be considered variants of atherectomy devices and finally, delivery devices to deliver medications, implants, and devices such as other interventional devices performing functions listed above as well as guiding elements including catheters and various types of guiding and interventional wires, imaging catheters and wires, contrast media, oxygenation elements, sensing instruments, radiation delivery elements, protective and shielding devices, downstream safety devices and others. Embodiments may be configured to be portable, disposable or reusable and may be, for example, electrically/electronically-, mechanically-, hydraulically-, pneumatically- and/or manually-, powered, controlled and operated.

DETAILED DESCRIPTION

Figure 1:
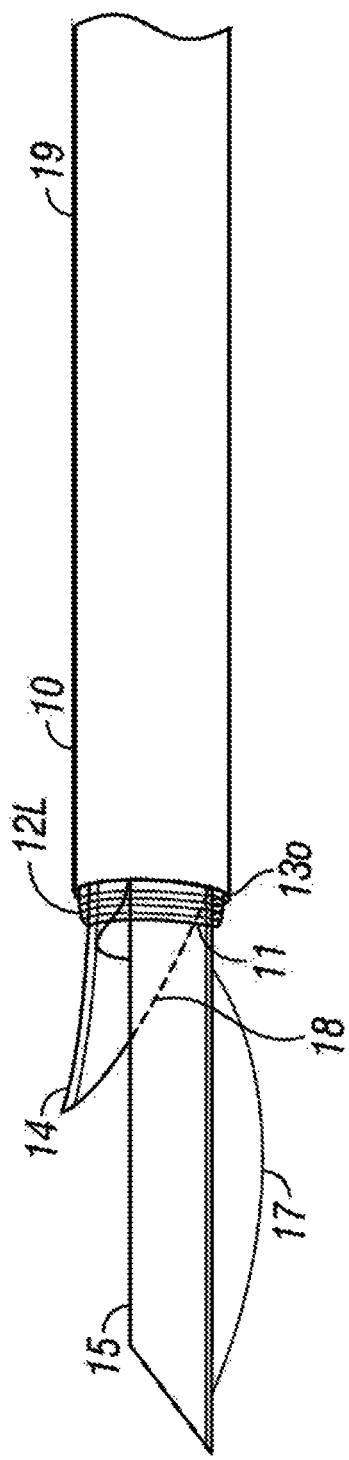
FIG. 1 is a perspective side view of a combined work element including an excisional device and a coaxial expansion device according to one embodiment.

Reference will now be made in detail to the construction and operation of implementations of the embodiments illustrated in the accompanying drawings. The following description is only exemplary of the embodiments described and shown herein. The embodiments, therefore, are not limited to these implementations, but may be realized by other implementations.

According to embodiments, a device for material or tissue excision may be configured to remove intra-vascular materials, and may comprise a range of work element dimensions ranging from, for example, approximately 0.0065" to 0.249" diameter (⅓ French to 19 French), or other appropriate dimensions both larger and smaller depending on applications and field of use requirements. According to embodiments, an excisional device may comprise a single tube or a single tube at least partially disposed within a coaxially-disposed outer tube or tubes, which outer tube or tubes may comprise a fixed or removable distal scoopula(e) or beak(s). Additional components may include coaxially mounted expansion devices such as balloons and stents, of either the self-expanding or actively, forcibly expanded variety and each of these may include drug delivery variants as well as resorb-able (temporary) implant variants. A work element, according to one embodiment, may comprise one or more scoopulae and/or one or more beaks. Either may be fixed or articulable, sharpened or unsharpened at their tips or along their side axes, and combinations of the two may be interchanged, according to embodiments. In the case of either articulable beaks or scoopulae, the principles of action as described herein and according to embodiments may be similar or different to that used for one relative to the other.

Herein, beaks may refer to that portion of a work element whose primary functions may comprise coring, shaving or grasping to remove material, and may also be fixed, articulable, sharpened or unsharpened, and may have various features and shapes according to various embodiments. Beaks may comprise a longitudinal living hinge elements such that the beaks may be expanded "out of round" to a more flattened shape, or alternatively a more tubular shape than when at rest. Beak driving assembly or assemblies in the device may have operating characteristics and features to enable rotational speeds advantageously chosen to optimize "sweep" ultrasound imaging using mechanical array or at a different speed to increase the information provided with phased array imaging, for example and may include longitudinal and "off angle" sweep capabilities as they are articulated to "shine" ultrasound or light energy at various structures of interest. These capabilities can also be used to receive signals in return and/or for reference signal processing. These capabilities can also be used together with "light out, sound in" systems that combine light and sound efferent and afferent signal processing to increase information available using a combination of these modalities. These rotational, longitudinal "pullback" and angular speeds may be generally in the same range as useful cutting, pullback/advancement and angular speeds, or they may be outside that normal range and activated separately for diagnostic or other therapeutic procedures (radiation delivery, medication "painting", injecting or other delivery). Driving assembly or assemblies (hereafter, collectively "driving assembly" for ease of reference) for beaks may be controllable at the handle end of the device (e.g., outside the body) and can be quite sophisticated, reusable and electronically optimized for torque, rotational speed (rpm) and frequency (in the cases of translation, angular changes and oscillation motions). The driving assembly may also comprise variable control as needed and may also include the ability to halt work element motions at a part-off phase (a phase at which a cut or cored piece of tissue is separated from surrounding tissue), with automated rearward (proximal) translation for purposes of delivering excised materials (e.g., pieces of tissue) to a transport portion of the device where, according to one embodiment, vacuum along with fluid management flows and swirls may complete the rearward delivery into a serial collection magazine of the device. Driving mechanisms may also include delivery of electrical, mechanical, radiant, ultrasonic, electromagnetic, electron beam and simple magnetic, among other, energies distally to a work element area, whereby conversion or re-conversion to another energy form may be made in the work area. As examples, electrical energy may be delivered to a receiving electromagnetic device to mechanically actuate a distal element, or turbine power generated may be transmitted distally via inert gases or mechanical spinning of elements acting directly on a distal element or simply via fluids that may be present or introduced in the presence of spinning elements according to embodiments, that may function to both create vacuum at the distal work element area while also creating mechanical motion in another or the same element, such as a high speed, low torque rotational element such that simultaneous dissolution and sucking of debris such as clotted blood or particulate matter rearward and safely out of the work area may be accomplished. Yet another example is that an e-beam sent distally may be directionally by elements in the work area in which case energy is precisely redirected and focused by embodiments, rather than converted to another form of energy per se. Multiple energies such as "light in, sound out" technologies among others, combining more than one modality to interrogate an area and supply more detailed information based on the modalities utilized in such a combination may be, at the same time, delivered, received and in some cases advantageously altered by elements of the present embodiments.

In general, a scoopula may be a portion of the work elements of the device or may be a separate structure from the work element. A scoopula may be characterized by an elongated portion of their morphology, and may have among their principle functions to define and/or isolate a work area within a vascular structure, and may for that purpose be fixed or articulable, with sharpened or unsharpened edges, and with a variety of shapes, according to various embodiments. In one embodiment, the scoopula may for example, refer to a beak element in combination with an elongated half-round cutout section (not necessarily exactly "half" of the whole tubular section) where a portion of a tubular section proximal to a beak element has part of its wall removed, as described and shown herein. Additionally, both scoopulae and beaks may be primarily designated for rotation at low speeds, whereas beaks may be configured for rotation at speeds varying, for example, from 1 revolution per minute (RPM) to several thousand RPM, according to embodiments. However, according to one embodiment, a scoopula may perform functions that are the same or similar to the functions discharged by the beak or beaks. According to one embodiment, a first scoopula may isolate a portion of a work area while a second scoopula may isolate a part of a work area in concert with the first scoopula, and either may be used to core or shave materials as though it or they were a beak or beaks. Another work element having articulable beaks, according to one embodiment, may be configured to capture and remove materials in the thus isolated work area. In this manner, an operator need not be limited to using a beak versus a scoopula at any stage of an intervention, based on the demands of the operation, including for example specific functions or vascular anatomic limitations for which one or the other may be better suited, to be performed and the objectives to be achieved with the present device 10 and the accessories thereto.

Embodiments of devices comprising variations of scoopula(e) may be configured to isolate the working surface(s) from the flow surfaces. In use in a vascular lumen, for example, this means that the lumen and/or potential lumen (tight stenoses and complete occlusions, whether chronic or acute) space will be protected before and additionally as soon as there is sufficient space to permit blood flow, including gently forced flow for the purposes of downstream oxygenation and nutrition, introduction of imaging equipment, and natural flows based on driving pressures relieved by new or widened lumens. This space (the lumen space) is isolated from the working space so that any elements that are released during removal actions will be prevented from impairing flow in the protected flow lumen of the vessel being widened in caliber. This space will be utilized such that vacuum may be maximized in the working side of the vessel as defined by the scoopula, and also in certain embodiments, while protecting the flow side—an embodiment may simultaneously press against the wall on the flow side (opposite to the working side) causing the working side of a catheter to be pressed against the lesion side of the vessel so that the elements on the working side of a device may be held precisely at the desired depth (for example for removing as much or little of a lesion as may be optimal for various considerations such as transport, degree of aggressiveness, rate of removal, particulate size of the material being removed, as the working beak element(s) are given purchase). Embodiments also provide a stable, geometrically straight reference platform. This reference platform may be used to straighten a desired segment of a vessel such that a uniform depth of lesion material may be safely removed without the concern for asymmetrically removing deep-wall elements (for example in an otherwise naturally or as a result of disease, tortuous section of a vessel) that may lead to weakening, aneurism formation or even perforation during the procedure.

The scoopula thus may, according to one embodiment, serve as an isolating element, a reference platform, a delivery platform permitting downstream element introduction, a stabilizing element and as a preventer of distal embolization. Living hinge or hinges may be defined in one or more portions of the scoopula. These may include straight longitudinal (axial) curved longitudinal (spirals, complex diagonals, etc.) and crossways configurations, as defined by kerfs cut into the tube from which the scoopula may be constructed. Embodiments may utilize any of these for example, depending on particular function, radius and degree of flexion and/or deflection, for use in specific vascular anatomic considerations among other considerations (whether or not more than one scoopula is used for example). Such configurations may enable expansion, variable, controllable rigidity, and geometry changes that enable tailored cuts that function as tip deflections, as well as for the purpose of temporary or permanent vessel expansion, the resultant forces of which may advantageously be directed in a radial direction, and scaffolding prior to stenting implant procedures or as stand-alone therapeutic procedures such as angioplasty of vessels, advantageously without the inherent strength limitations and non-directional expansion (radially) of typical balloon angioplasty technologies. Advantageously, distal flow around and/or through such structures may be less restrictive than balloon technologies that occupy the entire cross-section of a vessel such as an artery. Even when, in certain cases, very narrow spaces for distal flows are provided in specialized balloon devices, these are significantly limited in practical application and make these devices necessarily bulkier and harder to maneuver as a consequence. In contrast, according to embodiments, flow rates can be significantly higher based on expansion methods free of relatively thicker material and inflation materials. These configurations may also be used to enhance isolation and flow control on the proximal and distal ends of the isolation (working, non-flow) chamber. The sides may also be controllable with these living hinges to enhance working chamber isolation control. The back-side of a scoopula may be configured to enable pressing the working side against the obstructive material. Such urging may be carried out with, for example, pontoon-type inflatables, struts that are themselves living hinge elements, and/or may be a portion of the existing beak-actuating tendons or may be separate elements, and/or may include structural living hinge portions that change the effective caliber and or geometrical configuration(s) of the device such that pressure may be applied in the direction opposite the obstructive material direction within a vascular structure. Spiral(s), lateral expansions (longitudinal scoopula living hinge(s)), and combinations of the above may all be incorporated into the scoopula or scoopulae, according to embodiments.

One embodiment is a device comprising two co-axially-disposed work elements. Whether a work element comprises of one or more scoopulae or beaks, or combinations thereof, two or more co-axially placed work elements (referred to herein as a complex work element) may have particular advantages with regard to cutting or coring efficiencies in certain tissue types or with certain obstruction matrices. For example, a first work element or portion thereof, may be configured as a tubular structure ending in a fixed or articulable scoopula. A second work element may be co-axially placed inside or outside of the first work element, and may comprise one or more articulable beaks. According to one embodiment, the beak driving assembly and the scoopula driving assembly (which may be one and the same) may differentially rotate the first and second work elements such that the beak or beaks of the first work element may be driven in rotation at a first speed and/or direction and the scoopula or scoopulae of the second work element may be driven in rotation at a second rotational speed and/or direction that may be different from the first rotational speed and/or direction. In such an embodiment, open beaks may be extended distally along the length of the scoopula, and the beaks rotating differentially (at different speeds or in different directions, relatively) may create a shearing action between edges of the beak(s) and the sides of the scoopula (e), for example. Additionally, as the beaks are extended distally up to and even beyond the end of the extended portion of the scoopula(e), the scoopula(e) may serve as a tissue or obstruction anchoring mechanism, and cutting efficiency of the beak tips may be greatly enhanced as a result. As a second example, and according to one embodiment, a complex work element may be composed of work elements comprising two or more beaks. The ability to fine tune the length or degree of beak tip exposure of one work element versus the other, and the ability to fine tune the differential rim speeds (rim in this case referring to rotating beak tips as tissue or obstructions are penetrated and severed) enables a clean coring action accompanied by a gentle attack on such materials to be cored. If oppositely rotating work elements are used, the tissue or obstruction to be cored may be presented with, for example, sabre-shaped cutting surfaces that minimally expose the tissue to the cutting blades and vice versa for maximum coring efficiency, according to embodiments. Additionally, precisely opposed cutting action may advantageously prevent twisting of underlying deeper wall components, which is a known risk factor for tearing, dissection and other unfavorable tissue disruptions with resulting complete occlusion and flow obstruction, as well as frank vessel wall perforation, often requiring emergency open surgical intervention. Even without discernable acute events, deeper subclinical tissue disruption may lead to more aggressive healing responses in time leading to thrombus formation during the initial recovery period and restenosis due to intimal or deeper, hyperplasia of a vessel during the more extended recovery period. A stable scoopula edge in combination with a rotating inner or outer cutting element, according to embodiments, achieves this favorable effect (non-twisting cutting action) as may two or more oppositely rotating, separate beaks or scoopulae with their crossing distal edges, according to other embodiments. These are all included in various embodiments herein as are other elements that further stabilize complex work elements, for example, backside struts among others (asymmetry of expansion forces as another example).

An embodiment may include a coaxially mounted expansion device such as a simple balloon that is inflated to its expanded state, or may be of the pre-compressed variety, expanding upon release by removing an outer diameter-constraining sheath.

An embodiment may include a coaxially mounted expansion and drug delivery device such as a drug-eluting balloon, wherein the balloon may be covered by an outer sheath that seals an exposed edge or edges such that upon placement in a desired location for example in a vascular structure or other area where delivery is advantageously prevented from occurring prior to a point in time when it is desirable to release a drug from the delivery vehicle. An example of this is in the vascular system where it is desirable to shield a drug delivery device from fluids, to prevent premature elution of an active ingredient such as a drug.

One embodiment of a coaxial, de-bulking (atherectomy for example), pre-treatment device combined with a drug delivery balloon coaxially mounted has a peel-back covering enabling a gentle removal of a covering, fluid tight sealing membrane to isolate a drug delivery balloon and its active agents from being scraped or dissolved off before reaching the desired location. The combination of a pretreating (de-bulking) device with an immediately available expansion and delivery device enables efficient and efficacious pre-treatment, post-expansion and drug delivery in a single device to simplify a procedure, while minimizing potential downstream ischemic time.

Another embodiment is similar in that a coaxial de-bulking device is loaded with a coaxial stent that can be delivered following removal of obstructing material from a vessel wall before delivering a stent to the pre-treated location for example. In this way, an efficient procedure can be performed with a single device, the device can be equipped with a covering sheath to protect a stent, whether the stent is of the self-expanding or actively expanded variety and also regardless of whether the stent has drug-delivering capability or is of a resorb-able variety. In these embodiments, an outer covering sheath may perform more than a single function as described. Additionally, more than one such stent may be mounted coaxially on a device according to embodiments.

As used throughout this disclosure, work elements may comprise one or more tubes, and the terms "inner" and "outer" tubes may be used with reference to a single work element, or in reference to two or more co-axially located work elements (or "complex work elements", as used herein), each of which may comprise one or more tubes to enable their specific function. A coaxially-disposed outer tube, according to one embodiment, may also comprise one or more coatings. According to one embodiment, an outer tube may comprise a stainless-steel hypodermic tubing ("hypo tube"). Such a stainless hypo tube, according to one embodiment, may be provided with (e.g., laser) cuts to define a monolithic distal assembly that defines beaks, a living hinge that attaches the beak(s) to the generally tubular body of the device or that homogeneously spans between the beak(s) and the generally tubular body of the device. According to one embodiment, cuts in the hypo tube may define one or more tendons configured to actuate the beak(s). The cuts in the hypo tube may also define one or more tendon actuation tabs or body portion actuation tabs that enable actuation (e.g., opening and closing) the beak(s) through the tendons or body portion, according to embodiments, and limit the travel thereof. The tendon actuator tab(s) or body portion tab(s) may be located at any location along the length of the hypo tube. According to one embodiment, portions of the tube may be rigid. According to another embodiment, laser cuts along the proximally extended body portion of the tube may enable flexibility over its entire length or one or more portions thereof. The device may also comprise materials other than stainless steel, such as plastics or other suitable materials, which may incorporate the features of the beak(s), tendon(s), and, according to embodiments, tendon actuation tab(s) or an internal tube actuator element. Similar elements, structures, features and functionality contained in this disclosure are disclosed in co-pending and commonly assigned U.S. patent application Ser. No. 13/973,898 entitled "SOFT TISSUE CORING BIOPSY DEVICES AND METHODS"; U.S. patent application Ser. No. 14/050,771 entitled "SOFT TISSUE CORING BIOSPY DEVICES AND METHODS"; U.S. patent application Ser. No. 62/052,070 entitled "SOFT TISSUE BIOPSY OR EXCISIONAL DEVICES AND METHODS"; US patent application Ser. No. 62/052,591 entitled "IN-SITU MATERIAL DELIVERY DEVICES AND METHODS"; and U.S. patent application No. 61/876,977 entitled "TISSUE CORING BIOPSY DEVICES AND METHODS", the entire disclosures of which are hereby incorporated herein in their entirety.

FIG. 1 is side view of a multi-component assembly 10 comprising an inner work structure constructed of a single tube with an articulated beak 14 and fixed (in terms of flexion) scoopula 15, according to one embodiment. As previously described, the features of the inner work element may be cut from a single tube including the incorporated scoopula, which only needs to travel a short distance in concert with and relative to the flexible beak. Such a work element enables matching lips (of the beak and scoopula—not just at their tips), or tips only, with scissors mating at lateral lips overlap during, and at closure, and includes living hinge side-load applicator(s) 17, living tendons 18, travel limiting structures such as keystone element (not shown), and a movable scoopula 15. In this view, the tendon elements are also incorporated into the scoopula to enable simultaneous motion of the scoopula and the beak 14. According to embodiments, living hinge 17 features may include cuts to define their limits such as straight, longitudinal (axial), curved longitudinal (spirals, complex diagonals, etc.), and crossways type cuts or kerfs. Such configurations may thus enable expansion; variable, controllable rigidity; and geometry changes that enable the tailoring of the cutting action of the device, such as tip deflections. These features may also be used to enhance isolation on the proximal and distal ends of the isolation (working, non-flow) chamber that may be established intra-vascularly using a work element of this embodiment. The sides of the work element may also be controllable with these living hinge elements to enhance working chamber isolation control. The sides or lateral lips of the scoopula portion may be slightly tighter in terms of their tubular radius, such that upon flexion of the beak portion, a scissors action occurs advantageously to enhance separation of material from its attachment to host tissues. An additional component of multi-component assembly 10 shown in this view includes at least one or more of an expandable balloon element and an expandable scaffolding structure (stent in the vascular application, marker in a soft tissue biopsy application for example) either or both of which may elute active ingredients such as drugs or other chemicals for various purposes, such as for reducing restenosis (vascular application), local control of other proliferative activities (malignancies, infections, etc.) and to elute tracer substances (dyes, radioactive tracers, etc.). Also shown is the distal end, outer surface of an isolation sleeve 13(o), which is as shown in this illustration, sealed circumferentially to the distal end of a balloon element 11. These elements and structures herein described may be covered during advancement of device 10 through tight spaces or tortuous pathways by covering sleeve 19. Over-sleeve 19 may thus also protect the internal components during operation of the working end coring and shaving components described above including for example at least scoopula 15, beak(s) 14 and side-load applicator(s) 17.

Figure 2:
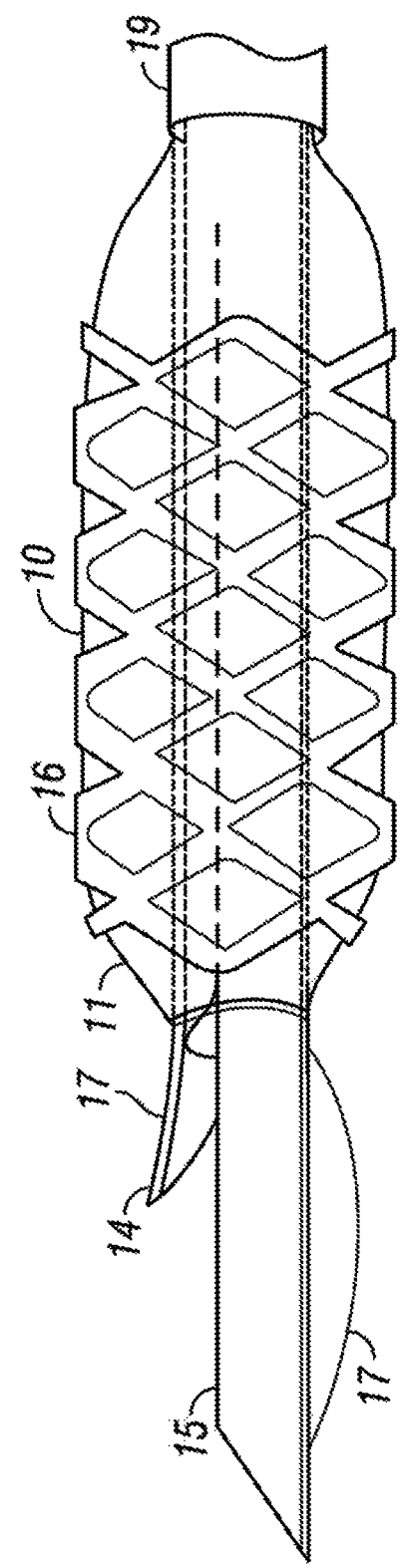
FIG. 2 is a perspective side view of a combined work element of an excisional device and a coaxial stent, according to one embodiment.

FIG. 2 illustrates another view of the multi-component assembly 10 of FIG. 1, this time with a covering sleeve 19 retracted exposing an expanded balloon 11 and a stent 16 also in expanded configuration. Note here that a stent 16 may be of the self-expanding variety and in such case, may be expanded and re-collapsed until in final position. At that point it may be dilated further to its final diameter (exerting no further significant pressure on vascular side walls for example) for complete apposition and vascular wall support. At the point of exposure to fluids (such as in a bloodstream) drug elution may commence, emanating from a balloon 11, a stent 16 or both for further local treatment(s). For example, one of the structures may contain a certain therapeutic agent while the other may elute a longer term therapy. (After treatment for example, a balloon 11 would normally be removed together with multi-component 10, while stent 16 may or may not be left behind for permanent implant or, if of the resorbing variety, may dissolve over time These structures may effectively operate to change the caliber of a vascular structure in multiple ways. The working end including coring and shaving components may remove obstructions and diseased intimal wall components, to a level that achieves a satisfactory luminal gain, given the elements shown enabling application of pressure applied in the direction opposite the obstructive material's location. Once a vascular wall is thus prepared for further treatments, one or more of the components including balloons, stents and drug delivery devices may be engaged to complete the full treatment(s).

Additional lumens or channels may be introduced used for contrast injection, flow augmentation, guide wire passage, imaging element passage such as phased-array "ultrasound on a wire" intravascular ultrasound (IVUS), fractional flow reserve (FFR) and instant wave-free ratio (iFR) devices among others, which are available on flexible wires ranging from about 0.009"-0.018" for example. These additional capabilities may be especially useful for immediate determination if the distal working components used to optimally prepare a vascular structure have been utilized to completion. In the case of such a multi-functional instrument as the present embodiment, it would be particularly desirable to immediately determine the ideal point in a procedure at which to deploy the other components such as balloons, stents and drug delivery capabilities. The scoopula itself or the beak elements can be a mounting point for imaging technologies such as optical coherence tomography (OCT). IVUS, near infrared and other imaging modalities and combinations to assess such factors as plaque vulnerability among others. Channels may be provided for fluid management including delivery and vacuum. A channel could be used for example, to over-pressurize a proximal segment while measuring iFR or FFR distally, to augment functional gradient measurement to gauge functional significance of stenotic segments before, during and after interventions, particularly in cases where it may be helpful to overcome limitations of abnormally decreased ambient intraluminal pressure as a result of impaired left ventricular function or sequential stenoses, and in cases where there may be a desire to avoid use of pharmacodynamic agents such as adenosine when performing functional studies. As mentioned each of these capabilities could be used to determine when to progress from one phase in a multi-phase procedure, using a single device to the next.

Figure 3:
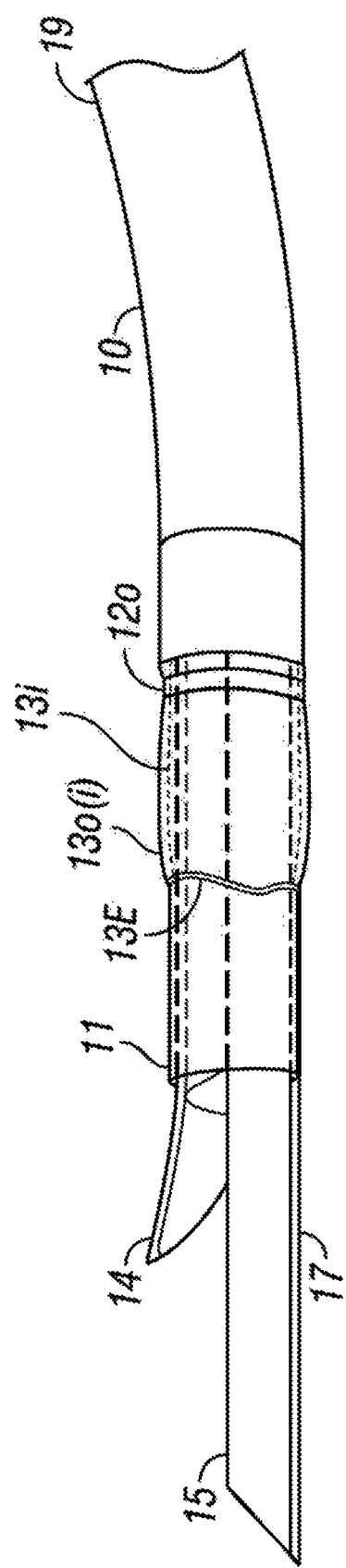
FIG. 3 is a view of a combined work element including an excisional device and a coaxial, partially uncovered drug delivery device, according to one embodiment.

FIG. 3 shows a multi-functional, multi-component device 10 similar to those in FIGS. 1 and 2, in this case illustrating a configuration that would follow ideal pre-treatment (de-bulking a vascular structure from diseased portions and other obstructions, such as thrombus, plaque and other abnormalities). In this configuration the next phase has already commenced, showing partial exposure of, for example, a drug eluting balloon 11, accomplished in this example by retracting over-sleeve 19, which itself is attached at its distal end to sealed covering sleeve 13. Covering sleeve 13 is labeled 13(e), which designates the peeling back edge of sleeve 13. 13(oi) indicates that this surface had been an inner surface prior to being peeled back proximally by proximal retraction action of over-sleeve 19. Note that a dashed line designated 13(i) indicates that portion of a sleeve 13 that is still an inner surface, by virtue of it's not being inverted by peeling at that point in the action as depicted in FIG. 3. This action also releases, by back-peeling, a sticky, circumferential sealing surface 12 (for example—it may also simply be an elastic collar that is dragged back over the inverting sleeve 13, thus protecting the outer drug-containing surface(s) from being subjected to sheering or scraping forces) that acts as a sealing tape to isolate a surface treated, covered component (balloon, stent, etc.) preventing it from losing its therapeutic components to fluids or physical separation before these types or other types of actions are needed for release (delivery). Note that in FIG. 3 the sealing band is labeled 12(o) indicating that its surface that was once an inner surface indicated by, in FIG. 1, being labeled 12(i), is now an outer surface 12(o) by virtue of it being peeled back as attached outer sleeve 19 is retracted in a proximal direction. Note also that this peeling action may be reversible for original assembly or for re-collapsing a balloon (for example after drug delivery) or a stent as may be a desirable action following their use at the site of interest. In that case, a distal rolling action may be achievable by returning over-sleeve 19 distally to its starting position, covering the inner components again or for the first time, according to embodiments. Such a work element may be especially useful for getting all components into place in tight spaces, potential spaces, tortuous vessels or more densely packed soft-tissue spaces and where rotation, oscillation or other actions of the distal work elements to excise materials may cause rubbing off of agents bound to inner balloons or stents, according to embodiments. Such other type of energized motion may comprise, for example, high frequency mechanical reciprocation and may include delivery of energies ranging among the medically useful electromagnetic frequencies. The bottom tray may constitute one pole of a bipolar-energized system for example, while other components of the beak working element may constitute the other pole in order to enable high concentrations of energy delivered precisely and limited to only those surfaces intended for cutting. This embodiment may also be useful where shaving a thin layer from a surface may be desirable, especially since the top flexible beak would now no longer need to be constrained to matching a circular "beak" shape in front profile, such that the top surface (flexible beak element 14) could be a much-widened shape or may be shaped as a low, flat arch. This could have the effect of advantageously creating a controlled depth of skim while advancing the device along a tissue plane for shallow tissue harvesting for example. Likewise, more flattened profiles may permit increased flow around devices variously configured in low profile according to embodiments FIGS. 1, 2 and 3 thus illustrate side views of three distinctive, separately controllable and deployable elements that perform several distinct functions in various phases of a treatment plan, all of which are able to be performed with a single instrument maneuvered to a site just once potentially. Some of these actions include (side-load application) force-generation, directional shaving, isolation of drug-delivery elements, such that these components can loiter locally while awaiting the time when they can be engaged in the procedure to further augment luminal gain, scaffold an area, deliver active agents for example to a vascular or soft tissue wall or lumen according to embodiments. The first element may be a working beak or scoopula with a flexible beak element incorporated at its terminus (the latter in this example). The second element is an outer protective sleeve element, which by virtue of its supported column strength, may function as an intravascular guiding/protecting/advancing element. This element may also control exposure of inner components sandwiched between an inner tube, which itself comprises a monolithic work element that may be used to perform tissue removal and transport functions. The sandwiched components constitute a third, multifunctional collection of elements including for example, a drug-delivering balloon, a drug delivering permanent implant (such as a stent or a marker) or a dissolvable drug delivering element (absorbable stent for example, or an absorbable marker, which, once dissolved may indicate by external imaging or other indicating modalities (Geiger counter for example) that all active agents have been delivered. The second element, which is a sliding exposure sleeve may, like the other two elements be configured to differentially rotate, oscillate or be otherwise energized for cutting purposes. Its additional purpose therefor may be to control the exposure of the window while providing stability, variable rigidity and a "bumper" slider effect to prevent any unwanted vessel wall trauma that might otherwise occur if some of the sharp edges of other components were allowed to be exposed to vessel lining outside the desired work area. The desired exposure of the distal sharp or energized surfaces may for example be as small as 0.004" or less, which may constitute another means of controlling depth of cutting for example, as well as limiting the length of cutting/coring for additional safety purposes. This element also serves to control the length of the more rigid working length as well as controlling the length of exposure of side-load applicators (bowing members). Lastly, this sliding exposure control can be used to control the vacuum area and to help internalize excised tissue for transport proximally.

Other embodiments of a device 10, comprising complex work elements each of which may be single or double tube work elements, with single or multiple beaks, scoopulae, combinations of the two, and including exchangeable independent work elements or separate devices, introduced into the central lumen of such a device with complex work elements, may be envisioned by one skilled in the art and are thus considered within the scope of this disclosure.

The described embodiments may be formed of or comprise one or more biocompatible materials such as, for example, stainless steel or other biocompatible alloys, and may be made of, comprise or be coated with polymers and/or biopolymer materials as needed to optimize function (s). For example, the cutting elements (such as the constituent elements of a work element 13) may comprise or be made of hardened alloys or carbon fiber or other polymers or plastics, and may be additionally coated with a slippery material or materials to thereby optimize passage through living tissues of a variety of consistencies and frictions. Some of the components may be purposely surface-treated differentially with respect to adjacent components, as may be inferred herein in reference to a transporting tubular and storage component (not shown). The various internal or external components may be made of any suitable, commercially available materials such as nylons, polymers such as moldable plastics, and others. The handle may be configured in such a way as to make it easily adaptable to one of any number of existing guiding platforms, such as stereotactic table stages. The materials used in the present material delivery or removal device may also be carefully selected from a Ferro-magnetic standpoint, such that the present material delivery or removal device maintains compatibility with magnetic resonance imaging (MRI) equipment that is commonly used for material delivery or removal procedures. Vacuum/delivery assembly components may comprise commercially available vacuum pumps, syringes and tubing for connecting to the present material delivery or removal device, along with readily available reed valves for switching between suction and emptying of materials such as fluids which may be suctioned by vacuum components. The fluids collected by the embodiments of the present device in this manner may then be ejected into an additional external, yet portable, liquid storage vessel connected to the tubing of the present device, for safe keeping and laboratory cellular analysis.

While certain embodiments of the disclosure have been described, these embodiments have been presented by way of example only, and are not intended to limit the scope of the disclosure. Indeed, the novel methods, devices and systems described herein may be embodied in a variety of other forms. Furthermore, various omissions, substitutions and changes in the form of the methods and systems described herein may be made without departing from the spirit of the disclosure. The accompanying claims and their equivalents are intended to cover such forms or modifications as would fall within the scope and spirit of the disclosure. For example, those skilled in the art will appreciate that in various embodiments, the actual physical and logical structures may differ from those shown in the figures. Depending on the embodiment, certain steps described in the example above may be removed, and others may be added. Also, the features and attributes of the specific embodiments disclosed above may be combined in different ways to form additional embodiments, all of which fall within the scope of the present disclosure. Although the present disclosure provides certain preferred embodiments and applications, other embodiments that are apparent to those of ordinary skill in the art, including embodiments which do not provide all of the features and advantages set forth herein, are also within the scope of this disclosure. Accordingly, the scope of the present disclosure is intended to be defined only by reference to the appended claims.

What is claimed is:

1. A device, comprising:
   a first tube comprising a scoopula at a distal end thereof, the scoopula being configured to press against a wall of a vascular structure to isolate a work area within the vascular structure from areas proximal and distal thereto; and
   a second tube, co-axially disposed within the first tube and comprising an articulable beak at a distal end thereof the articulable beak being configured to selectively open and close against the scoopula and to cut tissue within the isolated work area;
   an expandable balloon that is mounted coaxially within the scoopula and that is configured to selectively expand away from the scoopula to the wall of the vascular structure;
   an isolation sleeve, the isolation sleeve being disposed over and comprising a circumferential seal to a distal end of the expandable balloon;
   an over-sleeve, co-axially disposed over and attached to the distal end of the isolation sleeve, the over-sleeve being configured to retract in a proximal direction, to release the circumferential seal of the isolation sleeve to the distal end of the expandable balloon, to peel back the isolation sleeve such that a portion of an initially interior surface thereof becomes a portion of an outer surface thereof and to gradually expose the expandable balloon to the vascular structure as the over-sleeve is retracted.

2. The device of claim 1, wherein the scoopula is articulable.

3. The device of claim 1, wherein the scoopula is formed of a first single tube from which material has been removed and wherein the articulable beak is formed of a second single tube from which material has been removed.

4. The device of claim 1, wherein the scoopula is configured to flex toward the wall of the vascular structure.

5. The device of claim 1, wherein the scoopula comprises a first scoopula and a second scoopula, the first and second scoopulae being operative to isolate the work area within the vascular structure.

6. The device of claim 1, wherein the second tube is configured to rotate independently of the first tube.

7. The device of claim 1, further comprising an expandable stent disposed over the expandable balloon and under the isolation sleeve.

8. A device, comprising:
- a first work element formed of a single first tube from which material is removed to form a scoopula at a distal portion thereof; and
- a second work element formed of a single second tube from which material is removed to form at least one articulable beak at a distal portion thereof, the second work element being placed within a lumen of the first work element;
- an expandable balloon;
- an isolation sleeve, the isolation sleeve being disposed over and comprising a circumferential seal to a distal end of the expandable balloon;
- an over-sleeve, co-axially disposed over and attached to the distal end of the isolation sleeve, the over-sleeve being configured to retract in a proximal direction, to release the circumferential seal of the isolation sleeve to the distal end of the expandable balloon, to peel back the isolation sleeve such that a portion of an initially interior surface thereof becomes a portion of an outer surface thereof and to gradually expose the expandable balloon to a vascular structure as the over-sleeve is retracted,
- wherein the first work element is configured to isolate a work area within a vascular structure from areas proximal and distal thereto and wherein the second work element is configured to cut tissue within the isolated work area.

9. The device of claim 8, wherein the first work element is configured to rotate and wherein the second work element is configured to rotate independently of the first work element.

10. The device of claim 8, wherein the at least one articulable beak is configured to articulate via a living hinge.

11. The device of claim 8, wherein the scoopula is configured to flex.

12. The device of claim 8, further comprising an expandable stent disposed over the expandable balloon and under the isolation sleeve.

\* \* \* \* \*